(12) United States Patent
Glajch et al.

(10) Patent No.: US 6,254,852 B1
(45) Date of Patent: Jul. 3, 2001

(54) POROUS INORGANIC TARGETED ULTRASOUND CONTRAST AGENTS

(75) Inventors: Joseph L Glajch, Nashua, NH (US); Alan P. Carpenter, Jr., Carlisle, MA (US); Edward H. Cheesman, Lunenberg, MA (US)

(73) Assignee: Dupont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/356,178

(22) Filed: Jul. 16, 1999

(51) Int. Cl.$^7$ .................................................. A61B 8/00
(52) U.S. Cl. ............................................... 424/9.52
(58) Field of Search ................... 424/9.52, 9.51, 424/489, 490; 600/458, 441; 428/402; 516/11, 77

(56) References Cited

U.S. PATENT DOCUMENTS

| | | |
|---|---|---|
| 3,505,785 | 4/1970 | Kirkland . |
| 3,782,075 | 1/1974 | Kirkland . |
| 4,131,542 | 12/1978 | Bergna et al. . |
| 4,265,251 | 5/1981 | Tickner . |
| 4,427,646 | 1/1984 | Olexa et al. . |
| 4,442,843 | 4/1984 | Rasor et al. . |
| 4,554,088 * | 11/1985 | Whitehead et al. ............... 252/62.54 |
| 4,572,203 | 2/1986 | Feinstein . |
| 4,578,079 | 3/1986 | Ruoslahti et al. . |
| 4,659,756 | 4/1987 | Rasor et al. . |
| 4,681,119 | 7/1987 | Rasor et al. . |
| 4,705,725 | 11/1987 | Glajch et al. . |
| 4,792,525 | 12/1988 | Ruoslahti et al. . |
| 5,086,069 | 2/1992 | Klein et al. . |
| 5,088,499 | 2/1992 | Unger . |
| 5,147,631 * | 9/1992 | Glajch et al. ....................... 424/9.52 |
| 5,217,705 | 6/1993 | Reno et al. . |
| 5,270,030 | 12/1993 | Vogel et al. . |
| 5,277,892 | 1/1994 | Rhodes . |
| 5,279,812 | 1/1994 | Krstenansky et al. . |
| 5,558,094 | 9/1996 | Quay . |
| 5,595,723 | 1/1997 | Quay . |

FOREIGN PATENT DOCUMENTS

| | | |
|---|---|---|
| 0122624 | 9/1988 | (EP) . |
| 0478328 | 1/1992 | (EP) . |
| 727225 A2 * | 8/1996 | (EP) ............................. A61K/49/00 |
| 9000178 | 1/1990 | (WO) . |
| 9003391 | 4/1990 | (WO) . |
| 9015818 | 12/1990 | (WO) . |
| 9213572 | 8/1992 | (WO) . |
| 9219272 | 11/1992 | (WO) . |
| 9312819 | 7/1993 | (WO) . |
| 9317719 | 9/1993 | (WO) . |
| 9323085 | 11/1993 | (WO) . |
| 9325244 | 12/1993 | (WO) . |
| 9400489 | 1/1994 | (WO) . |
| 9405269 | 3/1994 | (WO) . |
| 9407918 | 4/1994 | (WO) . |
| 9419024 | 9/1994 | (WO) . |
| 9422494 | 10/1994 | (WO) . |
| 9428942 | 12/1994 | (WO) . |
| 9640285 | 12/1996 | (WO) . |
| 9851282 | 11/1998 | (WO) . |

OTHER PUBLICATIONS

J. Bakan in The Theory and Practice of Industrial Pharmacy (L. Lachman, H. A. Lieberman, and J. L. Kanig, eds.) pp 412–429 (1986).
Van Wazer (1958) Phosphorus and Its Compunds, vol. 1, pp 419–770, Interscience Publishers, New York.
Reidmeyer et al. (1986) J. Non–crystalline Solids 85: 186–203.
Hedricks (1984) Glass Science and Technology, vol. 2, pp 149–168, (ed. Uhlmann and Kreidl) Academic Press.
Moser and Lennoff (1989) Chem. Eng. Comm. 83: 241–259.
Kawahashi and Matijevic (1990) J. of Colloid and Interface Science 143:103–110.
Ojima et al., 204th Meeting of the Amer. Chem. Soc., 1992, Abstract 44.
Hartman et a al., J. Med. Chem., 1992, 35, 4640.
A. Fischman et al., Semin. Nuc. Med., 1994, 24, 154.
W. Hoekstra, Curr. Med. Chem. 1998, 5, 195–204.
R. Haubner, Angew. Chem. Int. Ed. Eng. 1997, 36, 1374–89.
H. H. Weetall, *Adv. Mol. Cell Biol.*, 15A (1996) pp. 161–192).
Roy et al. (1956) J. Am. Ceram. Soc. 39: 434.
J. S. Sawyer, et al., *J. Med. Chem*, 1995, 38, 4411–4432.

* cited by examiner

Primary Examiner—Michael G. Hartley
(74) *Attorney, Agent, or Firm*—Peter L. Dolan

(57) ABSTRACT

Targeted ultrasound contrast agents are described. The contrast agents are porous particles of an inorganic material containing an entrapped gas or liquid and having an average particle diameter of about 0.05 to 500 microns. The outer surfaces of the particles incorporate a targeting ligand to target delivery of the contrast agent.

23 Claims, No Drawings

POROUS INORGANIC TARGETED ULTRASOUND CONTRAST AGENTS

FIELD OF THE INVENTION

The invention relates generally to targeted ultrasound contrast agents having porous particles of an inorganic material containing an entrapped gas or liquid and having an average particle diameter of about 0.05 to 500 microns. The outer surfaces of the particles incorporate a targeting ligand to target delivery of the contrast agent.

BACKGROUND OF THE INVENTION

Techniques for ultrasound imaging various parts of the body are well known. An ultrasonic scanner is placed on the body surface overlying the area to be imaged. The sound waves generated by the scanner are directed toward the area to be imaged. The scanner then detects sound waves reflected from the underlying area and translates the signal into images.

The acoustic properties of a substance, such as an organ system, will depend upon the velocity of the ultrasonic transmissions and the density of the substance. Changes in the substance's acoustic properties will be most prominent at the interface of components of the substance differing in density, such as solid, liquid, and gas components. When ultrasonic energy is transmitted through a substance, the changes in acoustic properties (e.g., density) of the substance cause changes in the reflection characteristics, resulting in a more intense sound reflection signal received by the ultrasonic scanner.

Ultrasound contrast agents are introduced into the body organ system being imaged using ultrasound, and there act to influence the ultrasound signal in a way that enhances the ultrasound image. The contrast agent may be ingested or injected into and perfuse the microvasculature of the tissue desired to be imaged, to provide clearer images of the tissue. Such ultrasound contrast agents may be useful in helping to diagnose diseases earlier and more accurately.

Liquid and solid contrast agents containing entrapped gas are known in the art. The microbubbles provided by these contrast agents act as sound wave reflectors because of the acoustic differences between the gas microbubble and surrounding liquid.

Feinstein, U.S. Pat. No. 4,572,203, describes "microbubbles" of about 6–20 microns diameter produced by sonication of certain viscous solutions, as ultrasound contrast agents. Feinstein also describes solid or semi-solid metal-containing microparticles, such as glass or graphite, not containing trapped air, small enough to pass through capillaries, as ultrasound contrast agents. Also illustrated are microspheres formed from an amino acid polymer matrix, such as albumin, with magnetic particles, such as magnetite ($Fe_3O_4$) embedded therein.

Tickner, U.S. Pat. No. 4,265,251, depicts the use of certain saccharide composition "microbubble" particles with a hollow gas-filled interior space as ultrasound enhancing agents.

Rasor and Tickner, U.S. Pat. Nos. 4,442,843, 4,657,756, and 4,681,119, illustrate aggregates of microparticles (of 1–50 micron diameter) of a solid material, which are soluble in blood, containing gas in the voids between the particles, or with gas adsorbed on the surface of the particle, or containing gas as an integral part of the internal structure of the particle, for use in ultrasound imaging. The following solid materials are used: various saccharides, NaCl, sodium citrate, sodium acetate, sodium tartrate, $CaCl_2$ and $AlCl_3$.

Hilmann et al., European Patent Application Publication Number 122,624, contains microparticles comprised of a solid surface-active substance, including various organic lipophilic compounds, with enclosed air, as ultrasound contrast agents. Also described is the combination of particles of the surface-active material and particles of a non-surface active material, such as sodium chloride, sodium citrate, sodium acetate, sodium tartrate, and various saccharides.

Glajch et al, U.S. Pat. No. 5,147,631, discloses porous particles of an inorganic material containing an entrapped gas or liquid. The materials disclosed include monomeric or polymeric borates, monomeric or polymeric aluminas, monomeric or polymeric carbonates, monomeric or polymeric silicas, monomeric or polymeric phosphates; and pharmaceutically acceptable organic or inorganic cationic salts thereof.

Unger, U.S. Pat. No. 5,088,499, describes the preparation of gas filled liposomes and their use as ultrasound contrast agents. These include materials which contain gases, gaseous precursors which can be activated by pH, temperature, or pressure and other solid and liquid contrast agents.

Quay, U.S. Pat. No. 5,558,094, describes the use of microbubbles comprised of specially selected gases. These gases included specific halocarbons which were alleged to have longer persistence in solution as free microbubbles and therefore could be useful as ultrasound contrast agents.

The contrast agents described above are proposed for general ultrasound contrast imaging of the vasculature and especially for heart imaging. In addition, the imaging of specific organs, systems, or other areas of the body would be useful for a variety of diagnosing specific disease states. Examples of this include the specific imaging or tumors, blood clots, and areas of infection in a directed manner.

Quay, et al., European Patent Application Number 96630007.1 ilustrates the use of compositions including a cell adhesion molecule (CAM) ligand which is incorporated into a desired molecule to form a conjugate. The CAM is incoporated in a surfactant or albumin carrier and also comprises a chemical with sufficiently high vapor pressure to be a gas at body temperature.

The present invention relates to targeted ultrasound contrast agents comprising inorganic porous particles useful for ultrasound imaging and a targeting ligand that directs the particles to a body organ or disease site. Such contrast agents may be an important adjunct in ultrasound diagnostic procedures, for example, for cardiovascular, oncologic, and gastrointestinal uses. The inorganic porous particles of the invention provide contrast for ultrasound imaging; i.e., the particles act to reflect ultrasound waves and thereby enhance the ultrasound signal when introduced into the organ system being imaged using ultrasound.

SUMMARY OF THE INVENTION

The present invention provides novel targeted ultrasound contrast agents, comprising: a pharmaceutically acceptable carrier and porous particles of an inorganic material having an average particle diameter of about 0.05 to 500 microns and containing entrapped gas or liquid, and containing, on the outside surface of the particle, a targeting ligand to target delivery of the contrast agent. The entrapped gas or liquid provides a suitable echogenic interface to enhance an ultrasound image.

The targeting ligand is attached to the porous inorganic particles by coating, adsorbing, layering, or reacting the outside surface of the particle with the targeting ligand. Representative targeting ligands include RGD-containing peptides, other compounds that bind to members of the integrin, selectin, and IgG receptor superfamilies as well as cell surface substances which cause white blood cells to move towards sites of infection/inflammation, i.e., fMLF and leukotriene receptors (LTA, B, C, $D_4$).

The porous inorganic particles of the invention may be coated with a variety of organic polymeric and lipid materials to control the stability, pharmacokinetics, targeting, and biological effects of the particles in vivo.

The porous inorganic particles of the invention are administered parentally or nonparentally with a pharmaceutically acceptable carrier to a person, to thereby enhance the ultrasound image of a tissue or organ system of that person.

DETAILED DESCRIPTION OF THE INVENTION

[1] In a first embodiment, the present invention provides a novel targeted ultrasound contrast agent, comprising: a pharmaceutically acceptable carrier and a particle of the formula:

P—L—T wherein;

P is a porous particle of an inorganic material having an average particle diameter of about 0.05 to 500 microns and containing an entrapped gas or liquid, L is absent or is a linker, and T is a targeting ligand.

[2] In a preferred embodiment, the inorganic material is selected from borates, aluminas, carbonates, silicates, silicas, aluminosilicates, and phosphates, and organic or inorganic cationic salts thereof, and monomeric and polymeric forms, and mixtures of monomeric and polymeric forms thereof.

[3] In a more preferred embodiment, the inorganic material is in a form selected from crystalline, amorphous, or a mixture of crystalline and amorphous.

[4] In another preferred embodiment, T binds to a target selected from a cytokine, selectin, integrin, immunoglobin superfamily, and cadherin.

[5] In another more preferred embodiment, T binds to a target selected from a GpIIb/IIIa receptor, fibrin, fibrinogen, thrombin, vitronectin, epithelial growth factor, vascular endothelial growth factor, platelet derived growth factor, and $LTB_4$ receptors.

[6] In an even more preferred embodiment, T binds to a target selected from a GpIIb/IIIa receptor, vitronectin, and $LTB_4$ receptors.

[7] In another preferred embodiment, L is a silane.

[8] In another more preferred embodiment, L is a silane of the formula:

$R^1$—O—Si$(R^2)(R^3)(CH_2)_m(O)_n(R^4)$ wherein m is 0, 1, 2, or 3, n is 0 or 1, $R^1$ is selected from $CH_3$, $CH_2CH_3$, $CH(CH_3)_2$, and $CH_2CH_2CH_3$, $R^2$ is selected from $CH_3$, $CH_2CH_3$, $CH(CH_3)_2$, $CH_2CH_2CH_3$, cyclopropyl, cyclobutyl, cyclopentyl, and cyclohexyl, $R^3$ is selected from $CH_3$, $CH_2CH_3$, $CH(CH_3)_2$, $CH_2CH_2CH_3$, cyclopropyl, cyclobutyl, cyclopentyl, and cyclohexyl, $R^4$ is selected from the group $C_{1-6}$ alkyl substituted with 1–2 $R^5$, $C_{2-6}$ alkenyl substituted with 1–2 $R^5$, phenyl substituted with 1 $R^5$, $C_{3-6}$ cycloalkyl substituted with 1–2 $R^5$, and glycidyl, and $R^5$, at each occurrence, is OH or $NH_2$.

[9] In another even more preferred embodiment, L, prior to conjugation with P and T is selected from (3-aminopropyl)dimethylethoxysilane and (3-glycidoxypropyl)dimethylethoxysilane.

[10] In another preferred embodiment the entrapped gas is selected from the group consisting of air, $O_2$, $N_2$, $H_2$, $CO_2$, He, Ne, Ar, $CF_4$, $C_2F_6$, $C_3F_8$, cyclo-$C_4F_8$, $C_4F_{10}$, $C_5F_{12}$, cyclo-$C_5F_{10}$, cyclo-$C_4F_7$ (1-trifluoromethyl), propane (2-trifluoromethyl)-1,1,1,3,3,3 hexafluoro, and butane (2-trifluoromethyl)-1,1,1,3,3,3,4,4,4 nonafluoro.

[11] In another preferred embodiment the average particle diameter is 0.05 to 10 microns.

[12] In another preferred embodiment the porous particles have a single pore which is entirely or partially enclosed by a shell of the inorganic material.

[13] In another preferred embodiment the shell thickness is 1–45% of the average particle diameter.

[14] In another preferred embodiment the porous particles have a plurality of pores which are entirely or partially enclosed by the inorganic material.

[15] In another preferred embodiment the porous particles of inorganic material have a density of less than about 90% of the density of the inorganic material in a solid non-porous state.

[16] In another more preferred embodiment the porous particles of inorganic material have a density of less than about 60% of the density of the inorganic material in a solid non-porous state.

[17] In another even more preferred embodiment the porous particles of inorganic material have a density of 0.2% to 50% of the density of the inorganic material in a solid non-porous state.

[18] In another preferred embodiment the porous particles of inorganic material are substantially spherical in shape.

[19] In another preferred embodiment the inorganic material is selected from the group consisting of $SiO_2$, aluminum oxides, aluminum hydroxides, alkali salts of aluminosilicates, and $H_3BO_3$.

[20] In another more preferred embodiment the porous particles of inorganic material are coated with an organic material.

[21] In another even more preferred embodiment, the organic material is selected from the group consisting of ethylcellulose, hydroxypropylcellulose, methylcellulose, hydroxypropylmethylcellulose, polyvinylpyrrolidine, polyethylene, glycol, albumin, gelatin, starch, collagen, dextran, modified dextrans, polylactide/polyglycolide, polyalkylcyanoacrylates, polyacrylamide, cholesterol, phosphatidylcholine, phosphatidylinositol, polysorbates, polyethlyene ethers, polyethylene esters, and polyoxyethylene/polyoxypropylene block polymers.

[22] In another preferred embodiment the inorganic material is comprised of monomeric or polymeric forms, or a mixture of monomeric and polymeric forms, of phosphate.

[23] In another more preferred embodiment the inorganic material comprises monomeric or polymeric forms, or a mixture of monomeric and polymeric forms, of one or more alkali cation phosphate salts.

[24] In another even more preferred embodiment, the alkali cations are sodium, potassium, or calcium.

[25] In another preferred embodiment, the present invention provides a novel method of ultrasound imaging in a mammal, comprising: introducing to the mammal an amount of a targeted ultrasound contrast agent of the present invention effective to alter the ultrasound echogenicity of the target to be imaged.

The inorganic material useful in the present invention may exist in an amorphous or glass state or in a crystalline state or in a mixture of amorphous and crystalline forms. The inorganic material useful in this invention includes borates, aluminas, carbonates, bicarbonates, silicas, silicates, aluminosilicates, and phosphates in the form of monomeric salts or as polymeric or condensed forms, or as mixtures of monomeric and polymeric forms. Particles comprising mixtures of these materials are also expected to be useful in the present invention. Inorganic materials useful in the present invention include, but are not limited to, $SiO_2$, alkali salts of $CO_3^{2-}$ and $HCO_3^-$, alkali salts of $HPO_4^{2-}$, aluminum oxides and hydroxides, such as $Al_2O_3$, alkali salts of aluminosilicates, and $H_3BO_3$.

Phosphates, as the term is used herein, include various monomeric and condensed or polymeric crystalline forms and various noncrystalline or amorphous forms (including glass forms), as outlined below in Scheme I (adapted from Kirk and Othmer, Encyclopedia of Chemical Technology) and as described in Van Wazer (1958) Phosphorus and Its Compounds, Volume 1, pp 419–770, Interscience Publishers, New York, a standard textbook in the field of phosphate chemistry.

The preparation of various monomeric and condensed or polymeric forms of phosphate is appreciated by those skilled in the art of phosphate chemistry and is described in standard treatises on phosphate chemistry, for example, Van Wazer (1958) Phosphorus and Its Compounds, Volume 1, pp 419–770, Interscience Publishers, New York.

The term phosphates, as used herein, also includes derivatives of phosphates containing additional elements. For example, nitrogen can be incorporated into phosphate glasses to form oxynitride glasses, as described by Reidmeyer et al. (1986) J. Non-crystalline Solids 85: 186–203, the teaching of which is incorporated herein by reference. Nitriding the phosphate starting glass is expected to decrease the dissolution rate of the solid in water and increase the chemical stability of the solid. The preparation of phosphorus oxynitride glass by melting sodium metaphosphate in anhydrous ammonia to produce glasses containing up to 12 wt % nitrogen is described by Reidmeyer et al. Porous particles of oxynitride glasses and crystalline solids useful in the present invention can be prepared using the methods, described below.

Silicates and silicas, as used herein, includes any and all siliceous materials in the particulate form stated above. Typical silica material includes $SiO_2$, silicate-containing minerals, and synthetic silicates such as silica gels, powders, porous glass and those prepared by hydrolysis of calcium silicide or sodium silicate. The preparation of porous silica particles is described in Bergna and Kirkland, U.S. Pat. No. 4,131,542, Kirkland, U.S. Pat. No. 3,782,075, and Kirkland, U.S. Pat. No. 3,505,785, the contents of which are incorporated herein by reference.

The inorganic particles of the invention have the advantages of good mechanical stability and rigidity, which are important attributes lacking in other materials used as ultrasound contrast agents, such as sonicated albumin microspheres and perflurorocarbon emulsions. In addition, inorganic particles can be prepared and fabricated, using known techniques, into a variety of shapes, sizes, and extents of porosity, in order to obtain the most desirable contrast effects. In addition, inorganic porous particles can be prepared with a range of different solubilities in aqueous solution, such as a body fluid. The solubility of the inorganic porous particle may affect the rate of biodegradation and clearance of the agent in vivo and may, thereby, be an important property affecting the biological responses and toxicity associated with the ultrasound contrast agent.

The inorganic porous particles useful in the present invention comprise an inorganic solid material that encloses or partially encloses one or more pores or cavities. The porous particles of the invention contain an entrapped gas or liquid to provide a suitable echogenic interface to enhance an ultrasound image. The pore or pores may be completely enclosed or encapsulated by the inorganic material or may be partially enclosed and open to the surface of the particle. Thus, the particles are porous or hollow and contain an entrapped or partially entrapped gas or liquid in the pore or pores. Porous inorganic particles useful in this invention include particles having a single pore enclosed by a solid shell; i.e., hollow particles. Alternatively, the porous particle may have a single pore which is partially enclosed by a solid shell. The porous particles of the invention also include particles containing a plurality of pores. The pores may be interconnected and may connect to an opening at the surface of the particle. The particles may also contain pores which are completely enclosed and are not interconnected or open to the surface of the particle. Particles with non-interconnected and completely enclosed pores are known as closed cell foam type particles.

The inorganic particles useful in the present invention may range in size and shape or morphology. A variety of particle shapes are useful in the present invention. For example, the particles may range from roughly spherical shapes to rod-like shapes and may be regular or irregular in shape. The particle size, measured as the average particle diameter, should be in the range of about 0.01 microns to 1 millimeter. For irregular shaped particles, the term average particle diameter refers to the effective particle diameter or Stokes diameter of the particle. For injection or parenteral administration, the particles are preferably about 0.2–10 microns in diameter. For non-parenteral administration, such as ingestion, larger particles may be acceptable or preferred.

For purposes of tissue perfusion, the porous inorganic particle should preferably be about 0.2, 0.4, 0.6, 0.8, 1, 2, 3, 4, 5, 6, 7, 8, 9, or 10 microns in diameter and thereby small enough to pass through capillaries, which are about 8 to 10 microns in diameter, so as to perfuse the tissue. The porous inorganic particles of the invention should be small enough to permit their passage through capillaries without being filtered out and capable of perfusing the tissue and produce an enhanced ultrasound image that is of resolution sufficient to distinguish, for example, between well perfused and poorly perfused tissue for the detection and diagnosis of ischemia.

The porous gas-containing inorganic particles of the invention should have a density that is less than about 90, 80, 70, or 60% of the density of the solid nonporous inorganic material, preferably less than 60% of the density of the solid nonporous inorganic material. The density of the gas-containing porous inorganic particles of the invention is preferably about 0.2, 0.4, 0.6, 0.8, 1, 5, 10, 20, 30, 40, or 50% of the density of the non-porous inorganic material. The pore diameter may vary depending on the size of the particle and the number of pores, to achieve the preferred particle density. Thus, the pore size may range from about 20 angstrom to 500 microns. The pore diameters may be about 20, 100, 200, 300, 500, 1000 or 2000 angstroms for porous particles having a plurality of pores. For porous particles having a single pore, the thickness of the solid shell may vary. The shell thickness may be about 1–45% of the diameter of the particle. Thus, for porous particles having a single pore (i.e., hollow particles) having a particle size of about 0.2, 1, 10, 100, 200, 300, 400, or 500 microns, the pore size may correspondingly be about 0.2, 1, 10, 100, 200, 300, 400, or 500 microns.

The porous inorganic particles typically have a specific surface area of about 1, 10, 50, 100, 200, 500, 1000, or 1500 $m^2/g$. Because the porous inorganic particles of the present invention are modified on or near the outer surface the effective (i.e., derivatizable) surface area includes only the outer surface of the porous particle. Thus, it is only a small portion of the specific surface area of the porous particle. Typically, the effective surface area is less than 10 $m^2/g$ of porous particle. The porous inorganic particles of the invention may have a gas volume per gram of particle of greater than 0.05 mL/g, and preferably about 0.05, 0.1, 1, 5, 10, 20, 30, 40, or 50 mL/g.

Porous inorganic particles of the invention, useful as ultrasound contrast agents, may be prepared using standard methods for the preparation of porous particles. For example, porous inorganic particles may be prepared using standard methods involving the spraying of a metal salt solution into a furnace at elevated temperatures, such as standard spray drying, evaporation decomposition, high temperature aerosol decomposition, or drop-generator procedures.

The spray-drying procedure, as applied for the preparation of porous silica particles is described in Bergna and Kirkland, U.S. Pat. No. 4,131,542, the teaching of which is incorporated herein by reference. Similar procedures can be used for the preparation of porous particles composed of other materials including borates, aluminates, carbonates, phosphates, and mixtures thereof.

The drop-generator process for preparing high precision glass spheres is described by Hedricks (1984) Glass Science and Technology, volume 2, pp 149–168, (ed. Uhlmann and Kreidl) Academic Press, the teaching of which is incorporated herein by reference.

The high temperature aerosol decomposition (HTAD) process is described by Moser and Lennhoff (1989) Chem. Eng. Comm. 83: 241–259, the teaching of which is incorporated herein by reference. This procedure involves the spraying of a metal salt solution into a tube furnace at elevated termperatures, resulting in solvent evaporation, salt decomposition, and metal oxide ceramic particle formation. The HTAD of Moser and Lennhoff may be used for the synthesis of metal oxide particles having a range of surface areas and a range of particle morphologies, from nearly perfect hollow spheres to fragmented particles. By controlling the HTAD reactor conditions, materials having the desired morphology (spheres or fragmented particles), high or low surface area, phase purity, compositional purity, pore size distribution, and aqueous solubility may be obtained.

Hollow inorganic particles (i.e., particles having a single pore) may also be prepared by the process of coating a template or core particle composed of a material, such as polystyrene latex, with the inorganic material to form a shell around the core particle, and then subsequently removing the template or core material. Removal of the core can be achieved, for example, by heating and calcination of the core material. In such a process, the inorganic particle size, pore size, and thickness of the inorganic shell can be controlled quite precisely. Such a process of preparing hollow spherical particles is described by Kawahashi and Matijevic (1990) J. of Colloid and Interface Science 143:103–110.

The gas in the pore or pores of the porous inorganic particle may be a pure gas or mixture of gases, such as air.

For example, elemental gases such as $O_2$, $N_2$, $H_2$, He, argon, and other noble gases, and other light gases, such as $CO_2$, $CF_4$, or $C_2F_6$, $C_3F_8$, $C_4F_{10}$, and other fluorocarbon gases are expected to provide useful ultrasound contrast properties. The gases may be incorporated into the pores of the particles, for example, by exchange at high temperature and/or high pressure. Preferably the perfluorocarbon have less than six carbon atoms, e.g., $CF_4$, $C_2F_6$, $C_3F_8$, cyclo-$C_4F_8$, $C_4F_{10}$, $C_5F_{12}$, cyclo-$C_5F_{10}$, cyclo-$C_4F_7$ (1-trifluoromethyl), propane (2-trifluoromethyl)-1,1,1,3,3,3 hexafluoro, and butane (2-trifluoromethyl)-1,1,1,3,3,3,4,4,4 nonafluoro. Also preferred are the the corresponding unsaturated versions of the above compounds, for example $C_2F_4$, $C_3F_6$, the isomers of $C_4F_8$. The halogenated versions of hydrocarbons, where other halogens are used to replace F (e.g., Cl, Br, I) would also be useful, but may not be as desirable as the perfluorinated versions. Also, mixtures of these gases, especially mixtures of perfluorocarbons with other perfluorocarbons and mixtures of perfluorocarbons with other inert gases, such as air, $N_2$, $O_2$, He, would be useful. In addition to gases, liquids with boiling points below 37° C. can also be used. Examples of these can be found in Quay, U.S. Pat. No. 5,595,723, the contents of which are herein incorporated by reference.

The porous inorganic particles useful in the present invention may have a range of solubility in aqueous solution. Porous inorganic particles of any desired solubility can be obtained in several ways. The solubility can be controlled by selection of the desired particle surface area, the particle shell thickness, and/or the type of solid used in the particle. The inorganic particles may be comprised of a relatively insoluble solid, such as silicate materials, or may be relatively soluble in aqueous solution. For example, as discussed below, the solubility of phosphate materials can be controlled by the temperature and heating time used to prepare various amorphous or crystalline forms of phosphate material.

The porous inorganic particles must have a sufficiently slow dissolution rate in aqueous solution so as to exist in vivo following administration for at least about 1–30 minutes to provide enough time for the imaging procedure to be performed. For certain imaging applications, such as cardiovascular applications, where the contrast agent is administered parenterally, it may be desirable to use particles which are relatively soluble in serum or other body fluid. Porous inorganic particles having slower dissolution rates (i.e., reduced solubility) or insoluble particles, such as silica or alumina particles, may be desired for other uses, such as gastrointestinal imaging applications.

The porous inorganic particles of the present invention are modified on or near the outer surface of the particles to include a targeting ligand, i.e., a biologically active molecule or cell adhesion molecule. The biologically active molecule can be a protein, antibody, antibody fragment, peptide or polypeptide, or peptidomimetic that is comprised of a recognition sequence or unit for a receptor or binding site expressed at the site of the disease, or for a receptor or binding site expressed on platelets or leukocytes. The exact chemical composition of the biologically active molecule is selected based on the disease state to be diagnosed, the mechanism of localization to be utilized, and to provide an optimium combination of rates of localization and clearance.

Targets to which the targeting ligand can be selected to bind to include a wide variety of molecules including cytokines, selectins, integrins, immunoglobulin (Ig) superfamily and cadhedrins.

Cytokines are cellular regulatory proteins. They are produced by specific cells in response to a variety of stimuli and they can influence the behavior of target cells. They may act systemically or locally. Examples of cytokines include: Angiogenin, Epidermal growth factor, erythropoietin, Fibroblast Growth Factor (FGF), FGF basic, FGF-3, FGF-4, FGF-5, FGF-6, FGF-7, vascular endothelial growth factor (VEGF), platelet derived growth factor (PDGF), placental growth factor (PlGF), granulocyte-colony stimulating factor, granulocytemacrophage colony stimulating factor, GROa/MGSA, hepatocyte growth factor, heparin binding epidermal growth factor, interferon (IFN), IFNa/B, IFNd, insulin-like growth factor (IGF), IGF-I, IGF-II, interleukin (IL), IL-1a, IL-1b, IL-1ra, IL-2, IL-3, IL-4, IL-5, IL-6, IL-7, IL-8, IL-9, IL-10, IL-11, IL-12, IL-13, and IL-14.

Selectins, immunoglobulin (Ig) superfamily, and cadhedrins are expressed on cell surfaces and are involved in cell adhesion. Selectins have been implicated in the initial interactions between leukocytes and vascular endothelia leading to lymphocyte homing, platelet binding, and neutrophil extravasation. Examples of selectins include E-selectins, L-selectins, and P-selectins. Examples of immunoglobulin superfamily: Intercellular Adhesion molecule (ICAM), ICAM-1, ICAM-2, ICAM-3, Vascular cell adhesion molecule (VCAM), VCAM-1, VCAM-1 (alt), platelet endothelial cell adhesion molecule and mucosal addressin cell adhesion molecule. Examples of cadhedrins include CD44-H-CAM/GP90-Hermes.

Integrins are heterodimeric glycoprotein receptors consisting of a and b subunits that share a common b-subunit which combines non-covalently with an a-subunit to create functionally distinct receptors. One of their role is to integrate the ECM outside the cell with actin containing cytoskeleton inside the cell.

Integrin receptors are involved in adhesion in thrombus formation and restenosis, growth, tumor cell recognition and metastasis of cancer cells, angiogenesis, autoimmune diseases, infection and inflammation. Thrombus formation is dependent on platelet aggregation. Platelet aggregation is in turn dependent on the binding of fibrinogen and other serum proteins to the integrin glycoprotein receptor IIb/IIIa located on the platelet plasma membranes.

Examples of integrins include the VLA family: VLA-11, VLA-2, VLA-3, VLA-4, VLA-5, VLA-6, bla7, bla8, Blav; the LEUCAM family; LFA-1 Mac-1 and p150.95; and the cytoadhesion family: CD41a, vitronectin receptor, $b_3a_v$, $b_4a_6$, $b_5a_v$, $b_6a_v$, $b_7a_4$, LPAM-1, $b_7a_{IEL}$, $b_8a_8$, and others.

For the purposes of this invention, the term thromboembolic disease is taken to include both venous and arterial disorders and pulmonary embolism, resulting from the formation of blood clots.

For the diagnosis of thromboembolic disorders or atherosclerosis, the biologically active molecule is selected from the group including the cyclic IIb/IIIa receptor antagonist compounds described in co-pending U.S. Ser. No. 08/218,861 (equivalent to WO 94/22494); the RGD containing peptides described in U.S. Pat. Nos. 4,578,079, 4,792,525, the applications PCT US88/04403, PCT US89/01742, PCT US90/03788, PCT US91/02356 and by Ojima et. al., 204th Meeting of the Amer. Chem. Soc., 1992, Abstract 44; the peptides that are fibrinogen receptor antagonists described in European Patent Applications 90202015.5, 90202030.4, 90202032.2, 90202032.0, 90311148.2, 90311151.6, 90311537.6, the specific binding peptides and polypeptides described as IIb/IIIa receptor ligands, ligands for the polymerization site of fibrin, laminin derivatives, ligands for fibrinogen, or thrombin ligands in PCT WO 93/23085 (excluding the technetium binding groups); the oligopeptides that correspond to the IIIa protein described in PCT WO90/00178; the hirudin-based peptides described in PCT WO90/03391; the IIb/IIIa receptor ligands described in PCT WO90/15818; the thrombus, platelet binding or atherosclerotic plaque binding peptides described in PCT WO92/13572 (excluding the technetium binding group) or GB 9313965.7; the fibrin binding peptides described in U.S. Pat. Nos. 4,427,646 and 5,270,030; the hirudin-based peptides described in U.S. Pat. No. 5,279,812; or the fibrin binding proteins described in U.S. Pat. No. 5,217,705; the guanine derivatives that bind to the IIb/IIIa receptor described in U.S. Pat. No. 5,086,069; or the tyrosine derivatives described in European Patent Application 0478328A1, and by Hartman et. al., J. Med. Chem., 1992, 35, 4640; or oxidized low density lipoprotein (LDL).

For the diagnosis of infection, inflammation or transplant rejection, the biologically active molecule is selected from the group including the leukocyte binding peptides described in PCT WO93/17719 (excluding the technetium binding group), PCT WO92/13572 (excluding the technetium binding group) or U.S. Ser. No. 08/140,000; the chemotactic peptides described in Eur. Pat. Appl. 90108734.6 or A. Fischman et. al., Semin. Nuc. Med., 1994, 24, 154; the leukostimulatory agents described in U.S. Pat. No. 5,277,892, and LTB4 antagonists described in co-pending application U.S. Ser. No. 08/943,659, the contents of which are herein incorporated by reference.

For the diagnosis of cancer, the biologically active molecule is selected from the group of somatostatin analogs described in UK Application 8927255.3 or PCT WO94/00489, the selectin binding peptides described in PCT WO94/05269, the biological-function domains described in PCT WO93/12819, Platelet Factor 4, the growth factors (PDGF, EGF, FGF, TNF MCSF or Il1-8), and vitronectin antagonists described in W. Hoekstra, Curr. Med. Chem. 1998, 5, 195–204, and R. Haubner, Angew. Chem. Int. Ed. Eng. 1997, 36, 1374–89, and references therein.

The biologically active molecule may also represent proteins, antibodies, antibody fragments, peptides, polypeptides, or peptidomimetics that bind to receptors or binding sites on other tissues, organs, enzymes or fluids. Examples include the β-amyloid proteins that have been demonstrated to accumulate in patients with Alzheimer's disease, T cell protein, atrial naturetic factor derived peptides that bind to myocardial and renal receptors, antimyosin antibodies that bind to areas of infarcted tissues, or nitroimidazole derivatives that localize in hypoxic areas in vivo.

In addition to RGD, other peptide fragments are implicated in cell adhesive phenomena: KGD, found in Barbourin; SPENP, found in Elegantin and von Willebrand factor; CS-1, its core, cyclic and optimized peptide sequences which are responsible for selective VLA-4 inhibition; PRARI, implicated in heparin binding domain and focal adhesion formation and Disagregin which is involved in fibronectin binding.

Antibodies including monoclonal and polyclonal antibodies to the GPIIb/IIIa receptor and peptides containing these sequences or a peptidomimetic equivalent of these sequences are also antagonists of the integrin receptors. Non-RGD integrin ligands include collagen, specific for $a_1b_1$, $a_2b_1$, and $a_3b_1$, laminin and kalinin, specific for $a_2b_1$, $a_3b_1$, and $a_6b_1$. V-CAM, specific for $a_4b_1$; ICAM-1 and ICAM-2, specific for $a_Lb_1$ and $a_Mb_1$. There are also non-RGD binding regions of fibronectin and fibrinogen.

Cell adhesion molecule ligands (CAM ligands or CAMLIG) or antagonists are molecules which specifically interact with cell adhesion molecules. CAM ligands useful in the present invention include oligosaccharides terminating in the Sialyl Lewis X (SLex) sequence: a-Sialic-acid (2→3)bGa1(1→4)[aFuc(1→3)bGlc-NAc-OR which bind to a number of selectins: MAdCAM-1, CD34 and GlyCAM-1 which bind to L-selectins; PSGL-1 which bind to a number of P-selectins; LFA-1, and Mac-1 which bind to various ICAM'2; VLA4 which binds to VCAM-1; PECAM-1 which binds to PECAM-1.

Other peptides which may serve as CAM ligands in this invention include those disclosed in WO 94/07918, WO 94/19024, WO 93/25244, WO 93/23085, and WO 94/28942 which are hereby incorporated by reference.

Attachment of the targeting ligand to the porous particle either directly or with a covalent or non-covalent tether should provide a site-directed ultrasound contrast agent whose selectivity is related to the binding coefficient and specificity of the ligand. One method of attaching a targeting ligand is to incorporate a silane bonded to a silica surface on the particle (for general principles, see "The preparation of immobilized proteins covalently coupled through silane coupling agents to inorganic supports," by H. H. Weetall, *Adv. Mol. Cell Biol.*, 15A (1996) pp. 161–192). If the particle itself is silica, the desired silane can be directly reacted with the particle to modify the surface.

Useful silanes are those to which a targeting ligand can be attached. Preferably, the silane contains an amino group, an epoxy group, or a diol moiety (e.g., —(CH(OH)—CH$_2$(OH)). Silanes contemplated for use as linkers are of the formula:

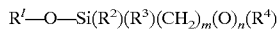

wherein m is 0, 1, 2, or 3, n is 0 or 1, $R^1$ is $C_{1-3}$ alkyl, $R^2$ is $C_{1-6}$ alkyl or $C_{3-6}$ cycloalkyl, $R^3$ is $C_{1-6}$ alkyl or $C_{3-6}$ cycloalkyl, $R^4$ is selected from the group $C_{1-6}$ alkyl substituted with 1–2 $R^5$, $C_{2-6}$ alkenyl substituted with 1–2 $R^5$, phenyl substituted with 1 $R^5$, $C_{3-6}$ cycloalkyl substituted with 1–2 $R^5$, and glycidyl, $R^5$, at each occurrence, is OH or NH$_2$. Examples of silanes which may be used include, but are not limited to 4-aminobutyldimethylmethoxysilane, 4-aminobutyltriethoxysilane, (aminoethylaminomethyl) phenethyltrimethoxysilane, N-(2-aminoethyl)-3-aminopropylmethyldimethoxysilane, N-(2-aminoethyl)-3-aminopropyltrimethoxysilane, N-(2-aminoethyl)-3-aminopropyltris(2-ethylhexoxy)silane, N-(6-aminohexyl) aminopropyl-trimethoxysilane, 3-(1-aminopropoxy)-3,3-dimethyl-1-propenyl-trimethoxysilane, 3-aminopropyltris (methoxyethoxyethoxy)silane, 3-aminopropylmethyldiethoxysilane, 3-aminopropyldiisopropylethoxysilane, 3-aminopropyltriethoxysilane, 3-aminopropyltrimethoxysilane, 3-aminopropyltris (trimethylsiloxy)silane, (3-aminopropyl) dimethylethoxysilane, (3-glycidoxypropyl)bis (trimethylsiloxy)methylsilane, 3-glycidoxypropyldiisopropylethoxysilane, (3-glycidoxypropyl)methyldiethoxysilane, 3-glycidoxypropylmethyldiisopropenoxysilane, 3-glycidoxypropyltrimethoxysilane, and (3-glycidoxypropyl)dimethylethoxysilane. Preferably, the silane contains a linear alkyl linkage between the silane and the amino group, epoxy group, or diol moiety. Preferably the silane is (3-aminopropyl)dimethylethoxysilane or (3-glycidoxypropyl)dimethylethoxysilane.

Glajch et al, U.S. Pat. No. 4,705,725, the contents of which are herein incorporated by reference, describe a number of methods of attaching silanes to particle surfaces. Once the silane has been attached to the particle, the selected targeting ligand can then be bonded to the amino, gylcidyl or diol group.

If the particle is not completely silica, another method would be to incorporate silanols (Si—OH groups) on or within the particle being prepared. This could be accomplished by preparing the major part of the particle in the presence of silica sol (small silica particles), which would then be physically incorporated within the matrix of the main substance (e.g., calcium phosphate particles). For example, one could prepare calcium carbonate particles with small amount (0.5–10%) of small silica sol (from 5 to 1000 nm) during the preparation. Some of these sol particles would be incorporated and provide the necessary Si—OH groups onto which subsequent silane reactions could be done.

The targeting ligand could also be attached directly to the particle by first reacting an appropriate silane linker to the targeting ligand and then attaching the silane-ligand complex to the particle through the silicon bond on the complex. For example, an acidic group on the targeting ligand could be bonded to the amino portion of (3-aminopropyl) dimethylethoxysilane and then the complex could be bonded to the particle through the ethoxysilane portion.

The number of targeting ligands per particle can vary from 1 to a maximum dependent upon the surface area and size of the particle and the number of activatable groups on the surface of the particle. As one of ordinary skill in the art would recognize, the number of ligands desired per particle will depend on a number of factors including the size of the ligand and the affinity of the ligand for its target. Thus, when a high affinity targeting ligand is being used, fewer ligands need to be attached to the particle than when a low affinity targeting ligand is being used. The number of ligands attached to the particle will also depend on the number of activatable surface molecules (e.g., silanols) present on the surface of the particle. It is preferable that 1, 2, 3, 4, 5, 10, 15, 20, 25, 30, 35, 40, 45, or 50% of the activatable surface molecules are derivatized with a targeting ligand with or without a linker (e.g., a silane linker). More preferably, 10, 11, 12, 13, 14, 15, 16, 17, 18, 19, or 20% of the activatable silanols are derivatized. For example, if about 8 $\mu$M/m$^2$ of activatable silanols are present on a silica particle, then it would be desirable for 0.05, 0.1, 0.2, 0.4, 0.6, 0.8, 1.0, 1.2, 1.4, 1.6, 1.8, or 2.0 $\mu$M/m$^2$ to be derivatized.

The porous inorganic targeted particles of the present invention are administered with an acceptable carrier to a person to enhance the contrast and resolution of ultrasound imaging of the tissue or organ system that is being targeted and imaged. Thus, the inorganic particles must have acceptable biocompatibility and toxicity properties in humans. The biocompatibility criteria will depend in part on the type of ultrasound imaging application and route of administration of the ultrasound contrast agent. For example, the biocompatibility criteria may be different for gastrointestinal administration than for parenteral administration of the contrast agent.

Physiologically acceptable pharmaceutical carrier fluids are used to transport and preferably stabilize the suspension of the particles (prevent sedimentation), and retard the dissolution of the particles. Useful carrier fluids include, but are not limited to water; aqueous solutions of one or more physiologically acceptable inorganic salts, such as physiological buffered solutions; aqueous solutions of mono- or disaccharides, such as galactose and lactose; and physiologically acceptable monofunctional or polyfunctional alcohols or their aqueous solutions. Also included are carrier fluids which enhance the adherence of the contrast agent to the organ or tissue walls or surface. Suitable pharmaceutical carriers are described in Remington's Pharmaceutical Sciences, Mack Publishing Co., a standard reference text in this field.

The porous inorganic particles of the invention may be coated with an organic material, such as those materials described below, to control the stability, pharmacokinetics, targeting, and biological effects of the particles in vivo. Such coating is preferably done before attachment of the targeting ligand, but in some cases may be done afterwards. Coating or microencapsulation of the particles can be used to enhance their stability in the formulation, to prevent aggregation, to alter their tissue distribution in the body and their elimination from the body, to reduce toxicity or enhance effectiveness, to reduce the adherence of biological materials which trigger immune reactions or thromboembolic reactions, to control the dissolution rate of soluble particles, and to control the permeation of water and other substances into and out of the particle matrix, among other uses.

Methods for coating solid particles are described by J. Bakan in The Theory and Practice of Industrial Pharmacy (L. Lachman, H. A. Lieberman, and J. L. Kanig, eds.) pp 419–429. The methods generally most useful for coating particles less than 100 micron approximate size include air suspension, coacervation-phase separation, multiorifice centrifugal, and solvent evaporation. The coating might vary in composition, thickness, and porosity, depending on the intended effect.

Representative organic materials to form the coating include organic polymeric substances including cellulose polymers such as ethylcellulose, hydroxypropylcellulose, methylcellulose, and hydroxypropylmethylcellulose, polyvinylpyrrolidone, polyethylene glycol, albumin, gelatin, starch, collagen, dextran and modified dextrans, polylactide/polyglycolide, polyalkylcyanoacrylates, polyacrylamide, lipids such as cholesterol, phosphatidylcholine, and phosphatidylinositol, and surfactants such as polysorbates, polyethylene ethers and esters, and polyoxyethylene/polyoxypropylene block polymers. The inorganic particles of the invention may also optionally be coated with a surface-active substance, such as those described by Hilman et al., European Patent Application Publication Number 122,624. Many of these coatings will also be useful for the attachment of targeting ligands through coating, adsorbing, covalent, or non-covalent bonding.

Other features of the invention will become apparent in the course of the following descriptions of exemplary embodiments which are given for illustration fo the invention and are not intended to be limiting thereof.

EXAMPLES

Example 1

An aqueous solution of sodium silicate is introduced into a spray drying apparatus or into a high temperature aerosol decomposition (HTAD) apparatus of the type described originally by Roy et al. (1956) J. Am. Ceram. Soc. 39: 434 and as reviewed in Moser and Lennhoff (1989) Chem. Eng. Comm. 83: 241–259.

The crust-forming step and the subsequent evaporation steps may be carried out at temperatures of less than about 250° C., in order to prevent any condensation, polymerization, or other chemical changes in the silica shell material during formation of the particle during the spray drying or HTAD process. The overall size of the resulting particles should be no greater than about 5–10 microns. The particles should be collected in a manner that attrition and exposure to moisture is avoided.

The resultant hollow silica particles are then heated in a temperature controlled furnace at a temperature and for a time that will produce condensed forms of silica. The temperature and duration of the heating of the porous partilces is selected such that the particles obtained have the desired solubility in aqueous solution.

The hollow particles so obtained after heat treatment were then reacted with an aminopropyl-dimethylethoxysilane as follows to produce a hollow particles with a modified surface. Four grams of hollow particles were heated overnight at 110° C. under vacuum (3 in. Hg) to remove adsorbed water, and then placed in a dry nitrogen atmosphere. To this solid was added 40 mL dry xylene, 5.2 μL pyridine, and 53 mg of (3-aminopropyl)dimethylethoxysilane. The mixture was refluxed at 138° C. for 72 h under slow nitrogen purge. The cooled reaction mixture was filtered and the particles washed with 500 mL each of toluene, methylene chloride, methanol, 50% methanol/water, and methanol, in that order. The material was refluxed for 30 min in fresh tetrahydrofuran and fresh acetone (40 mL of each solvent) to remove any unreacted silane. The particles were then dried at 110° C. in a vacuum oven.

The aminopropyl functionalized particles were then slurried in sufficient dimethylformamide (DMF) or acetonitrile-DMF mixture (3:1) in a rotating reactor to give a mobile slurry. To this is added 380 mg 2-(1H-benzotriazole-1-yl)-1,1,3,3-tetramethyluronium hexafluorophosphate (HBTU), 500 mg of 8-propyl-7-[3-[4-(4-fluorophenyl)-2-ethyl-5-hydroxyphenoxy]propoxy]-3,4-dihydro-2H-1-benzopyran-2-carboxylic acid (Cmpd 1, prepared as described in J. S. Sawyer, et. al., *J. Med. Chem,* 1995, 38, 4411–4432, which is known to bind with high affinity to the leukotriene B4 binding site on the neutrophil as a potent antagonist), and 375 μL of diisopropylethylamine.

1

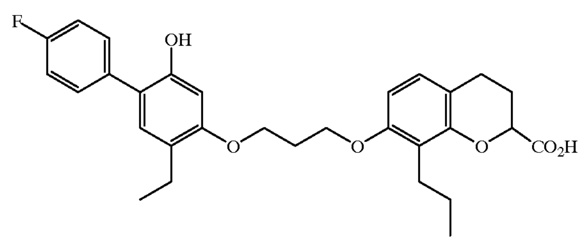

The slurry is agitated by slow rotation for 36 hours or until a picric acid test shows no free amine binding sites. The slurry is filtered, washed in turn with DMF, methylene chloride, methanol, 50% methanol/water, and acetone and then dried at 110° C. in a vacuum oven.

The resulting hollow particles were placed in a chamber and evacuated to remove air. The chamber was then backfilled with 1 atmosphere of perfluoropropane gas.

Example 2

An aqueous solution of sodium silicate is introduced into a spray drying apparatus or into a high temperature aerosol decomposition (HTAD) apparatus of the type described originally by Roy et al. (1956) J. Am. Ceram. Soc. 39: 434 and as reviewed in Moser and Lennhoff (1989) Chem. Eng. Comm. 83: 241–259.

The crust-forming step and the subsequent evaporation steps may be carried out at temperatures of less than about 250° C., in order to prevent any condensation, polymerization, or other chemical changes in the silica shell material during formation of the particle during the spray drying or HTAD process. The overall size of the resulting particles should be no greater than about 5–10 microns. The particles should be collected in a manner that attrition and exposure to moisture is avoided.

The resultant hollow silica particles are then heated in a temperature controlled furnace at a temperature and for a time that will produce condensed forms of silica. The temperature and duration of the heating of the porous partilces is selected such that the particles obtained have the desired solubility in aqueous solution.

The hollow particles so obtained after heat treatment were then reacted with a 3-glycidoxypropyl-dimethylethoxysilane as follows to produce a hollow particles with a modified surface. Four grams of hollow particles were heated overnight at 110° C. under vacuum (3 in. Hg) to remove adsorbed water, and then placed in a dry nitrogen atmosphere. To this solid was added 40 mL dry xylene, 5.2 µL pyridine, and 71 mg of (3-glycidoxypropyl) dimethylethoxysilane. The mixture was refluxed at 138° C. for 72 h under slow nitrogen purge. The cooled reaction mixture was filtered and the particles washed with 500 mL each of toluene, methylene chloride, methanol, and acteone, in that order. The material was refluxed for 30 min in fresh tetrahydrofuran and fresh acetone (40 mL of each solvent) to remove any unreacted silane. The particles were then dried at 110° C. in a vacuum oven.

The glycidoxylpropyl functionalized particles are then slurried in sufficient dimethylformamide (DMF) in a round-bottom flask with a nitrogen purge stream to give a mobile slurry. To this is added 610 mg of Cyclo-(D-Val-NMeArg-Gly-Asp-Mamb(5-Aca)) (Cmpd 2, see WO 94/22494, page 263 for a preparation of this molecule), and 375 µL of diisopropylethylamine.

2

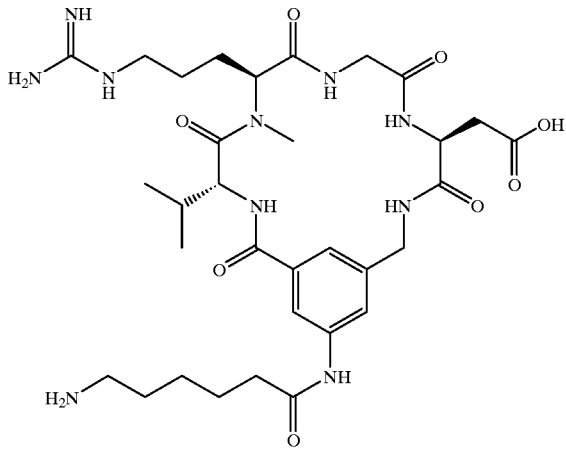

The slurry is heated to 80° C. with a nitrogen purge for 36 hours. The slurry is filtered, washed in turn with DMF, methylene chloride, methanol, 50% methanol/water, and acetone and then dried at 110° C. in a vacuum oven.

The resulting hollow particles were placed in a chamber and evacuated to remove air. The chamber was then back-filled with 1 atmosphere of perfluoropropane gas.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A targeted ultrasound contrast agent, comprising: a pharmaceutically acceptable carrier and a particle of the formula:

P—L—T wherein;

P is a porous particle of an inorganic material having an average particle diameter of about 0.05 to 500 microns and containing an entrapped gas or liquid;

L is absent or is a silane of the formula:

$R^1—O—Si(R^2)(R^3)(CH_2)_m(O)_n(R^4)$ wherein m is 0, 1, 2, or 3;

n is 0 or 1;

$R^1$ is selected from —$CH_2$—, $CH_2CH_2$—, —$CH(CH_3)$ $CH_2$—, and —$CH_2CH_2CH_2$—;

$R^2$ is selected from —$CH_3$, —$CH_2CH_3$, —$CH(CH_3)_2$, —$CH_2CH_2CH_3$, cyclopropyl, cyclobutyl, cyclopentyl, and cyclohexyl;

$R^3$ is selected from —$CH_3$, —$CH_2CH_3$, —$CH(CH_3)_2$, —$CH_2CH_2CH_3$, cyclopropyl, cyclobutyl, cyclopentyl, and cyclohexyl;

$R^4$ is selected from the group $C_{1-6}$ alkyl substituted with 1–2 $R^5$, $C_{2-6}$ alkenyl substituted with 1–2 $R^5$, phenyl substituted with 1 $R^5$, $C_{3-6}$ cycloalkyl substituted with 1–2 $R^5$, and glycidyl; and $R^5$, at each occurrence, is —O— or —NH—; and T is a targeting ligand.

2. A contrast agent according to claim 1, wherein the inorganic material is selected from borates, aluminas, carbonates, silicates, silicas, aluminosilicates, and phosphates, and organic or inorganic cationic salts thereof, and monomeric and polymeric forms, and mixtures of monomeric and polymeric forms thereof.

3. A contrast agent according to claim 2, wherein the inorganic material is in a form selected from crystalline, amorphous, or a mixture of crystalline and amorphous.

4. A contrast agent according to claim 1, wherein T binds to a target selected from a cytokine, selectin, integrin, immunoglobin superfamily, and cadherin.

5. A contrast agent according to claim 4, wherein T binds to a target selected from a GpIIb/IIIa receptor, fibrin, fibrinogen, thrombin, vitronectin, epithelial growth factor, vascular endothelial growth factor, platelet derived growth factor, and $LTB_4$ receptors.

6. A contrast agent according to claim 5, wherein T binds to a target selected from a GpIIb/IIIa receptor, vitronectin, and $LTB_4$ receptors.

7. A contrast agent according to claim 1, wherein L, prior to conjugation with P and T is selected from (3-aminopropyl)dimethylethoxysilane and (3-glycidoxypropyl)dimethylethoxysilane.

8. A contrast agent according to claim 1, wherein the entrapped gas is selected from the group consisting of air, $O_2$, $N_2$, $H_2$, $CO_2$, He, Ne, Ar, $CF_4$, $C_2F_6$, $C_3F_8$, cyclo-$C_4F_8$, $C_4F_{10}$, $C_5F_{12}$, cyclo-$C_5F_{10}$, cyclo-$C_4F_7$ (1-trifluoromethyl), propane (2-trifluoromethyl)-1,1,1,3,3,3 hexafluoro, and butane (2-trifluoromethyl)-1,1,1,3,3,3,4,4,4 nonafluoro.

9. A contrast agent according to claim 1, wherein the average particle diameter is 0.05 to 10 microns.

10. A contrast agent according to claim 1, wherein the porous particles have a single pore which is entirely or partially enclosed by a shell of the inorganic material.

11. A contrast agent according to claim 1, wherein the shell thickness is 1–45% of the average particle diameter.

12. A contrast agent according to claim 1, wherein the porous particles have a plurality of pores which are entirely or partially enclosed by the inorganic material.

13. A contrast agent according to claim 1, wherein the porous particles of inorganic material have a density of less than about 90% of the density of the inorganic material in a solid non-porous state.

14. A contrast agent according to claim 13, wherein the porous particles of inorganic material have a density of less than about 60% of the density of the inorganic material in a solid non-porous state.

15. A contrast agent according to claim 14, wherein the porous particles of inorganic material have a density of 0.2% to 50% of the density of the inorganic material in a solid non-porous state.

16. A contrast agent according to claim 1, wherein the porous particles of inorganic material are substantially spherical in shape.

17. A contrast agent according to claim 1, wherein the inorganic material is selected from the group consisting of $SiO_2$, aluminum oxides, aluminum hydroxides, alkali salts of aluminosilicates, and $H_3BO_3$.

18. A contrast agent according to claim 17, wherein the porous particles of inorganic material are coated with an organic material.

19. A contrast agent according to claim 18, wherein the organic material is selected from the group consisting of ethylcellulose, hydroxpropylcellulose, methylcellulose, hydroxypropylmethylcellulose, polyvinylpyrrolidine, polyethylene, glycol, albumin, gelatin, starch, collagen, dextran, modified dextrans, polylactide/polyglycolide, polyalkylcyanoacrylates, polyacrylamide, cholesterol, phosphatidylcholine, phosphatidylinositol, polysorbates, polyethlyene ethers, polyethylene esters, and polyoxyethylene/polyoxypropylene block polymers.

20. A contrast agent according to claim 1, wherein the inorganic material is comprised of monomeric or polymeric forms, or a mixture of monomeric and polymeric forms, of phosphate.

21. A contrast agent according to claim 20, wherein the inorganic material comprises monomeric or polymeric forms, or a mixture of monomeric and polymeric forms, of one or more alkali cation phosphate salts.

22. A contrast agent according to claim 21, wherein the alkali cations are sodium, potassium, or calcium.

23. A method of ultrasound imaging in a mammal, comprising: introducing to the mammal an amount of a targeted ultrasound contrast agent of claim 1 effective to alter the ultrasound echogenicity of the target to be imaged and performing an ultrasound scan to obtain an image.

\* \* \* \* \*